(12) United States Patent
Cesarini et al.

(10) Patent No.: US 7,922,737 B1
(45) Date of Patent: Apr. 12, 2011

(54) RECIPROCATING ROTARY ARTHROSCOPIC SURGICAL INSTRUMENT

(75) Inventors: Peter M. Cesarini, Londonderry, NH (US); Karen Drucker, Londonderry, NH (US); Rafal Jezierski, Londonderry, NH (US); Roger R. Cassidy, Methuen, MA (US)

(73) Assignee: Smith & Nephew, Inc., Memphis, TN (US)

( * ) Notice: Subject to any disclaimer, the term of this patent is extended or adjusted under 35 U.S.C. 154(b) by 1020 days.

(21) Appl. No.: 11/734,674

(22) Filed: Apr. 12, 2007

Related U.S. Application Data

(63) Continuation of application No. 09/983,810, filed on Oct. 26, 2001, now Pat. No. 7,226,459.

(51) Int. Cl.
*A61B 17/32* (2006.01)
*A61B 10/00* (2006.01)

(52) U.S. Cl. .................. 606/170; 606/180; 600/566

(58) Field of Classification Search .................. 606/170, 606/180; 600/564, 566, 567
See application file for complete search history.

(56) References Cited

U.S. PATENT DOCUMENTS

| | | | |
|---|---|---|---|
| 1,585,934 A | 5/1926 | Muir | |
| 2,708,437 A | 5/1955 | Hutchins | |
| 3,995,619 A | 12/1976 | Glatzer | |
| 4,203,444 A | 5/1980 | Bonnell et al. | |
| 4,316,465 A | 2/1982 | Dotson, Jr. | |
| 4,493,698 A | 1/1985 | Wang et al. | |
| 4,517,977 A | 5/1985 | Frost | |
| 4,601,290 A | 7/1986 | Effron et al. | |
| 4,649,919 A | 3/1987 | Thimsen et al. | |
| 4,867,157 A | 9/1989 | McGurk-Burleson et al. | |
| 4,940,061 A | 7/1990 | Terwilliger et al. | |
| 5,007,917 A | 4/1991 | Evans | |
| 5,106,364 A | 4/1992 | Hayafuji et al. | |
| 5,116,868 A | 5/1992 | Chen et al. | |
| 5,152,744 A | 10/1992 | Krause et al. | |
| 5,176,677 A | 1/1993 | Wuchinich | |
| 5,269,785 A | 12/1993 | Bonutti | |
| 5,304,118 A | 4/1994 | Trese et al. | |
| 5,312,399 A | 5/1994 | Hakky et al. | |
| 5,312,425 A | 5/1994 | Evans et al. | |
| 5,364,395 A | 11/1994 | West, Jr. | |
| 5,395,313 A | 3/1995 | Naves et al. | |
| 5,409,013 A | 4/1995 | Clement | |
| 5,425,376 A | 6/1995 | Banys et al. | |
| 5,429,601 A | 7/1995 | Conley et al. | |
| 5,456,689 A | 10/1995 | Kresch et al. | |
| 5,490,860 A | 2/1996 | Middle et al. | |
| 5,569,284 A | 10/1996 | Young et al. | |

(Continued)

OTHER PUBLICATIONS

Fishing Reel produced and sold by Shimano of Japan into the U.S. prior to Oct. 26, 2001, 7 pages.

*Primary Examiner* — Julian W Woo

(74) *Attorney, Agent, or Firm* — Fish & Richardson P.C.

(57) ABSTRACT

A surgical instrument includes a cutting member with an implement for cutting tissue, and a drive coupled to the cutting member to simultaneously rotate and translate the cutting member in response to a force applied to the drive. A method of cutting tissue includes positioning an outer member such that tissue is located within the outer member, engaging the tissue with an inner member, and simultaneously rotating and translating the inner member to cut the tissue. A tangential cutting force is applied to the tissue with the inner member to mechanically cut the tissue. The inner member is mechanically driven to undergo simultaneous rotation and translation.

6 Claims, 14 Drawing Sheets

U.S. PATENT DOCUMENTS

| | | | |
|---|---|---|---|
| 5,591,187 A | 1/1997 | Dekel | |
| 5,649,547 A | 7/1997 | Richart et al. | |
| 5,702,420 A | 12/1997 | Sterling et al. | |
| 5,741,286 A | 4/1998 | Recuset | |
| 5,741,287 A | 4/1998 | Alden et al. | |
| 5,775,333 A * | 7/1998 | Burbank et al. | 600/567 |
| 5,857,995 A | 1/1999 | Thomas et al. | |
| 5,873,886 A | 2/1999 | Larsen et al. | |
| 5,911,699 A | 6/1999 | Anis et al. | |
| 5,913,867 A | 6/1999 | Dion | |
| 5,925,055 A | 7/1999 | Adrian et al. | |
| 5,928,163 A | 7/1999 | Roberts et al. | |
| 6,004,320 A | 12/1999 | Casscells et al. | |
| 6,007,513 A | 12/1999 | Anis et al. | |
| 6,039,748 A | 3/2000 | Savage et al. | |
| 6,068,641 A | 5/2000 | Varsseveld | |
| 6,120,147 A | 9/2000 | Vijfvinkel et al. | |
| 6,132,448 A | 10/2000 | Perez et al. | |
| 6,203,518 B1 | 3/2001 | Anis et al. | |
| 6,217,543 B1 | 4/2001 | Anis et al. | |
| 6,224,603 B1 | 5/2001 | Marino | |
| 6,258,111 B1 | 7/2001 | Ross et al. | |
| 6,277,096 B1 | 8/2001 | Cortella et al. | |
| 6,632,182 B1 * | 10/2003 | Treat | 600/564 |
| 6,656,132 B1 | 12/2003 | Ouchi | |
| 6,712,773 B1 | 3/2004 | Viola | |
| 7,226,459 B2 * | 6/2007 | Cesarini et al. | 606/170 |
| 2003/0078609 A1 | 4/2003 | Finlay et al. | |

* cited by examiner

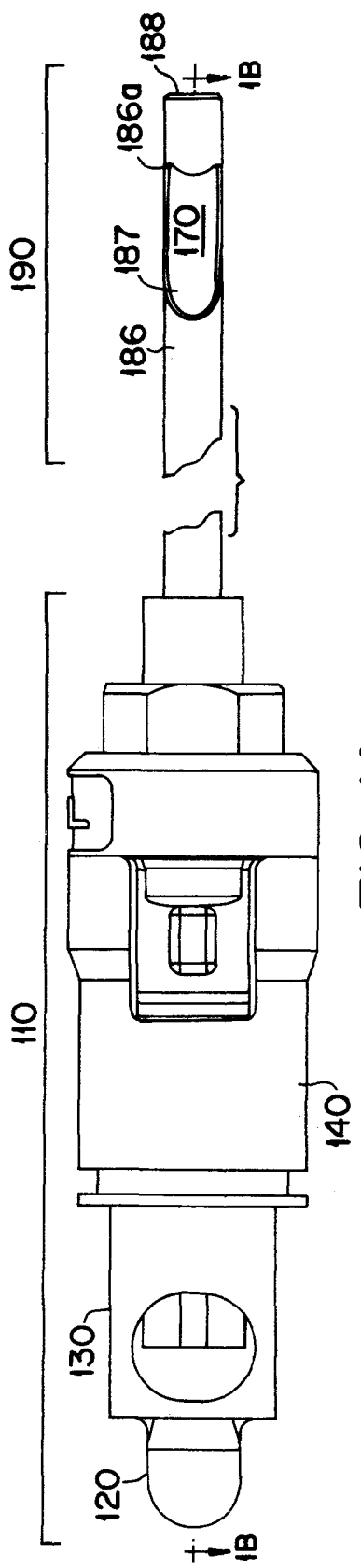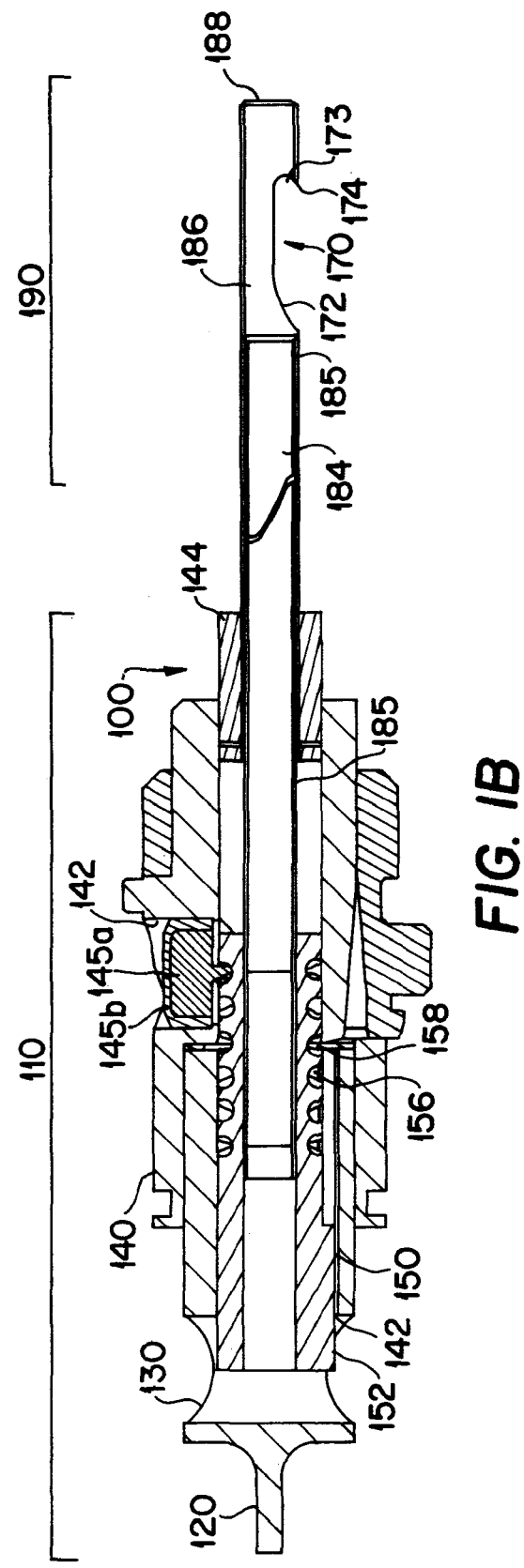
FIG. 1A
FIG. 1B

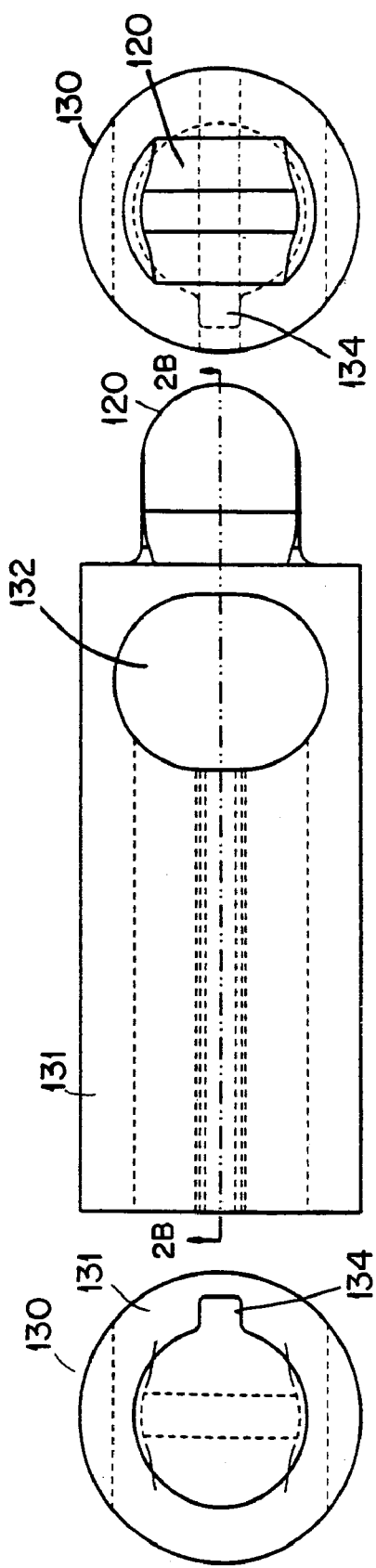

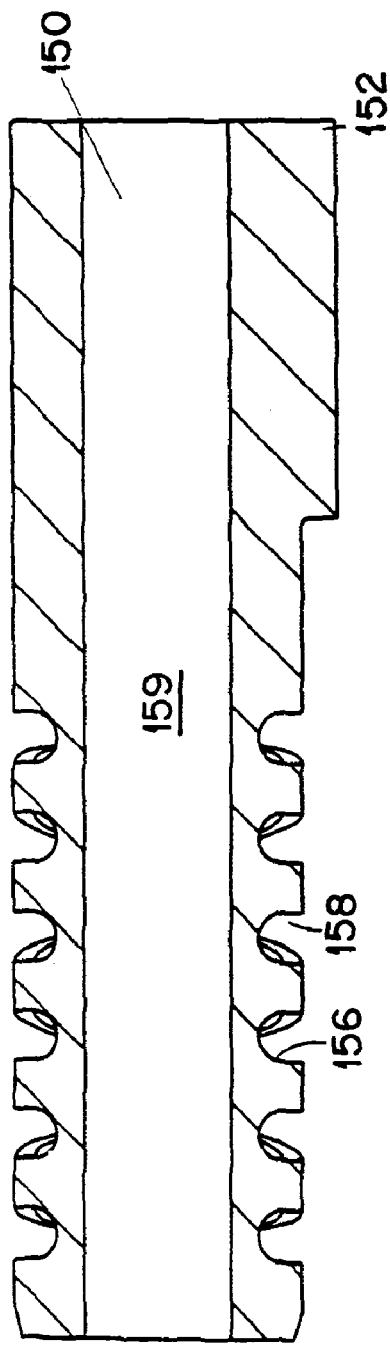
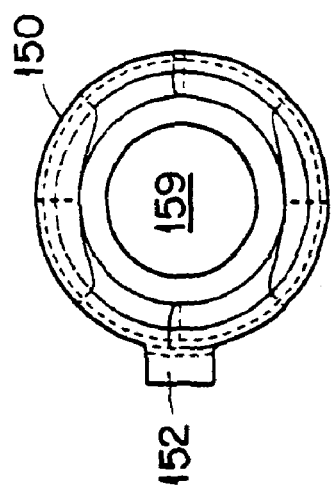
FIG. 3C
FIG. 3D

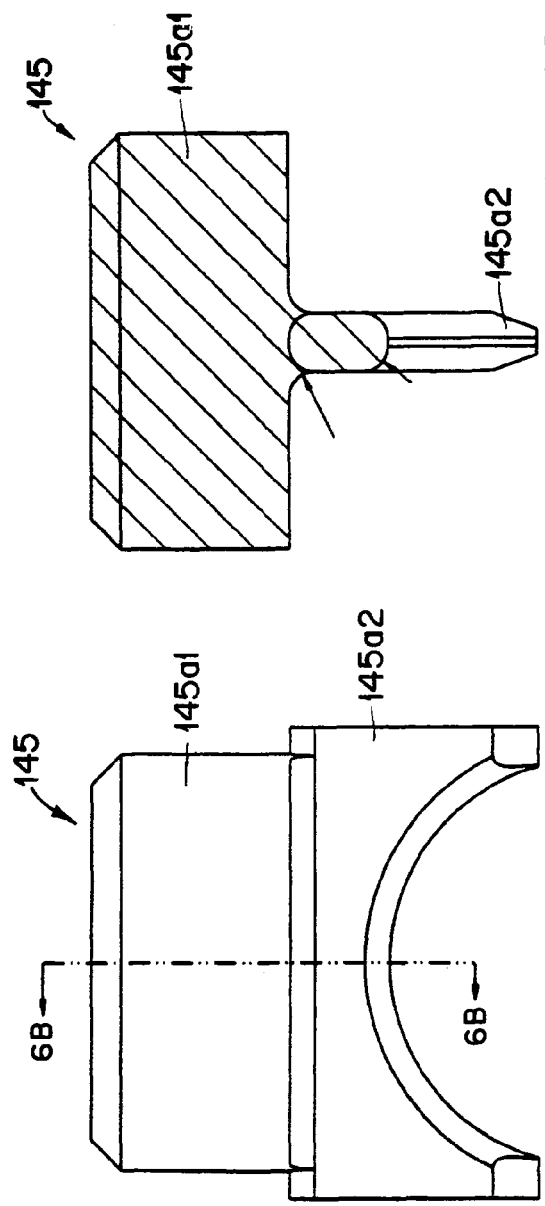

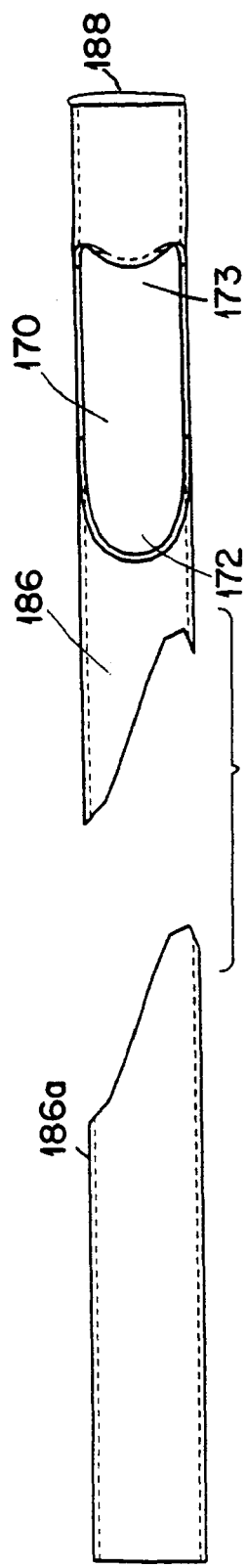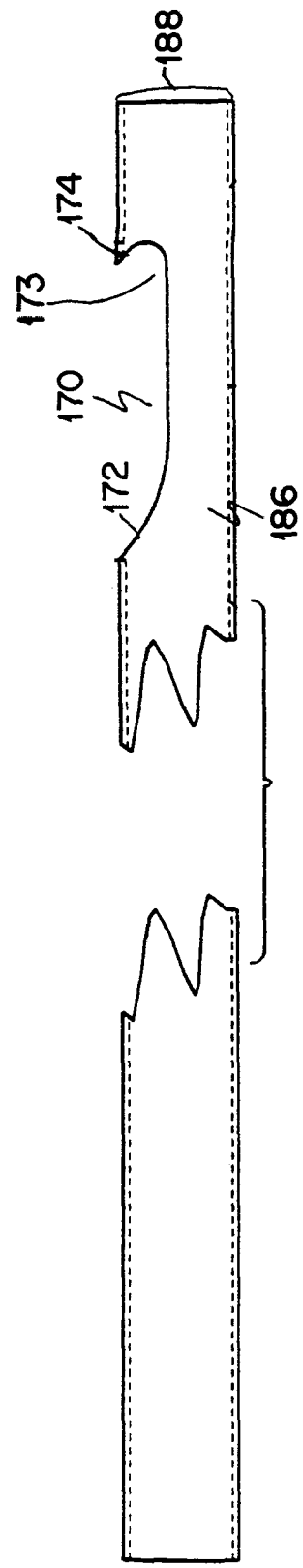

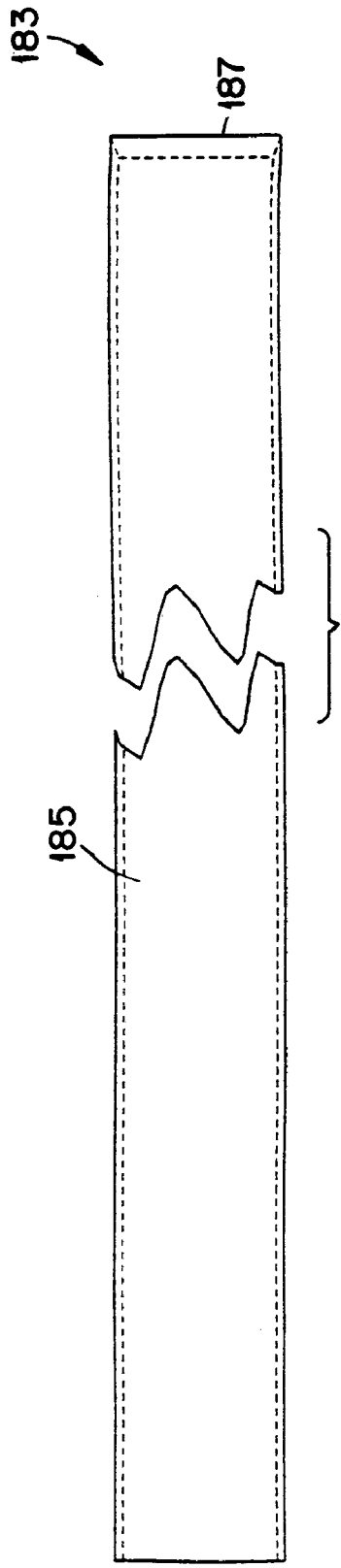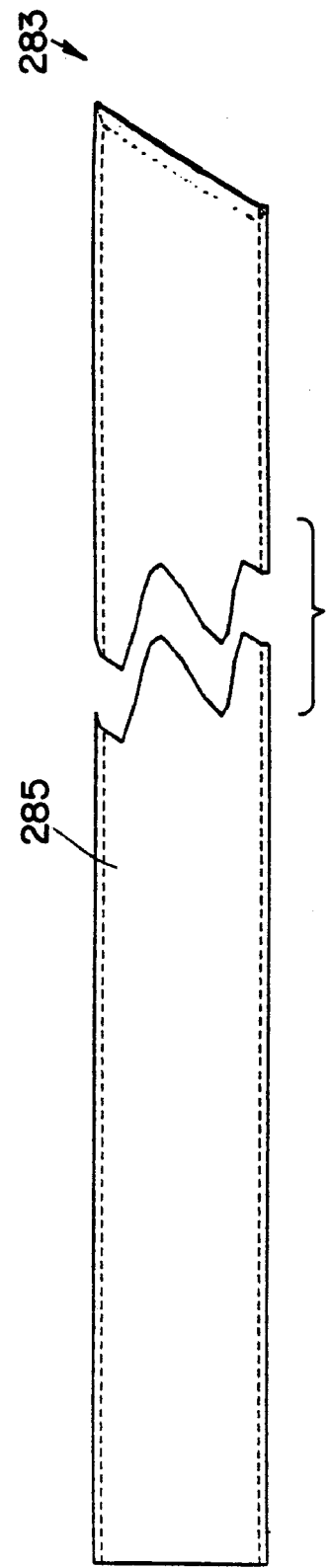

RECIPROCATING ROTARY ARTHROSCOPIC SURGICAL INSTRUMENT

CROSS REFERENCE TO RELATED APPLICATION

This application is a continuation of U.S. application Ser. No. 09/983,810, filed Oct. 26, 2001, which is incorporated herein by reference in its entirety.

TECHNICAL FIELD

This invention relates to rotary cutting surgical instruments, and more particularly, to a reciprocating rotary surgical instrument for cutting semi-rigid tissue.

BACKGROUND

Conventional arthroscopic surgical instruments generally include an outer tube and an inner member that rotates or translates axially within the outer tube. The outer tube and inner member may interact to create shear forces that cut tissue. This type of cutting is generally used to cut soft tissue, such as muscle, ligaments, and tendons.

SUMMARY

In one aspect, a surgical instrument includes a cutting member with an implement for cutting tissue, and a drive coupled to the cutting member to simultaneously rotate and translate the cutting member in response to a force applied to the drive.

One or more of the following features may be included in the surgical instrument. The drive is configured such that the cutting member reciprocates. The drive includes a drive member attached to the cutting member. The drive member includes a helical groove. The drive includes a translation piece disposed in the groove such that rotary driving of the drive member results in simultaneous reciprocation of the drive member relative to the translation piece.

In the illustrated embodiment, the drive includes an inner drive hub coupled to the drive member. The inner drive hub defines a slot and the drive member includes a key received in the slot rotary coupling the drive member to the inner drive hub such that the drive member rotates with the inner drive hub while being free to translate relative to the inner drive hub. The helical groove includes a left-hand threaded helical channel. The helical groove includes a right-hand threaded helical channel. The cutting member is attached to the drive member to move rotatably and axially with the member.

The implement is a chamfered cutting edge at a distal end of the cutting member. The chamfered edge is a straight cutting edge. Alternatively, the chamfered edge is an angled cutting edge.

The instrument includes an outer tubular member. The cutting member is received within the outer member. The outer member includes a cutting window disposed proximate to a tip of the outer member. The cutting window is an opening in the outer member exposing the cutting member to tissue. The cutting window has a U-shaped proximal end and a saddle-shaped distal end. The saddle-shaped distal end of the cutting window includes a hook.

The translation piece includes a follower received within the groove and a sealing cap over the follower. The follower is free to swivel relative to the sealing cap. The follower has an arched bridge shape. The translation piece is coupled to the drive member such that the translation piece is disposed in the helical groove and swivels to follow the helical groove as the drive member rotates.

In another aspect, a method of cutting tissue includes positioning an outer member such that tissue is located within the outer member, engaging the tissue with an inner member received within the outer member, and simultaneously rotating and translating the inner member to cut the tissue. One or more of the following features may be included. The translating is reciprocating. The outer member is oriented tangentially to the tissue.

In another aspect, a method of cutting tissue includes providing a surgical instrument having an outer member and an inner member received within the outer member for movement relative to the outer member, and applying a tangential cutting force to the tissue with the inner member to mechanically cut the tissue.

In another aspect, a method of cutting tissue includes applying a tangential cutting force to tissue with a member, and mechanically driving the member to undergo simultaneous rotation and translation. The method may include that the translation is reciprocation.

The cutting edge of conventional arthroscopic surgical instruments, such as rotary shears, have difficulty initiating a cut into semi-rigid tissue tend to bounce away from the tissue. Toothed edge geometry somewhat ameliorates this problem because the "teeth" attempt to pierce the tissue to initiate a cut. However, the efficiency of using "teeth" is limited and the limitations are more evident when cutting large volumes of semi-rigid tissue, such as meniscus or intrauterine fibroid tissue. The simultaneous rotating and reciprocating inner member of the surgical instrument of the invention overcomes these difficulties. The tangential approach to the tissue in the method of the invention limits the tendency of the instrument to bounce away from the tissue. In particular, the instrument and method provide a higher resection rate to shorten procedure length, during, e.g., fibroid and polyp resection.

The details of one or more implementations are set forth in the accompanying drawings and the description below. Other features will be apparent from the description and drawings, and from the claims.

DESCRIPTION OF DRAWINGS

FIG. 1A is a side view and 1B is a cross-sectional view taken along 1B-1B in FIG. 1A of a reciprocating rotary surgical instrument.

FIG. 2A is a top view, FIG. 2B is a cross-sectional view taken along 2B-2B in FIG. 2A, FIG. 2C is a distal end view, and FIG. 2D is a proximal end view of the inner drive hub of the reciprocating rotary surgical instrument of FIG. 1.

FIG. 3C is a cross-sectional view taken along 3C-3C in FIG. 3A, and FIG. 3D is a proximal end view of the helical member of the reciprocating rotary surgical instrument of FIG. 1.

FIG. 6A is a side view, FIG. 6B is a cross-sectional view taken along 6B-6B in FIG. 6A, and FIG. 6C is a top view of the follower of the translation piece of the reciprocating rotary surgical instrument of FIG. 1.

FIG. 8A is a top view and FIG. 8B is a side view of the outer member of the reciprocating rotary surgical instrument of FIG. 1.

FIG. 9 is a side view of the inner member of the reciprocating rotary surgical instrument of FIG. 1.

FIG. 11 is a side view of an alternate implementation of the inner member of a reciprocating surgical instrument.

Like reference symbols in the various drawings indicate like elements.

DETAILED DESCRIPTION

Figure 3A:
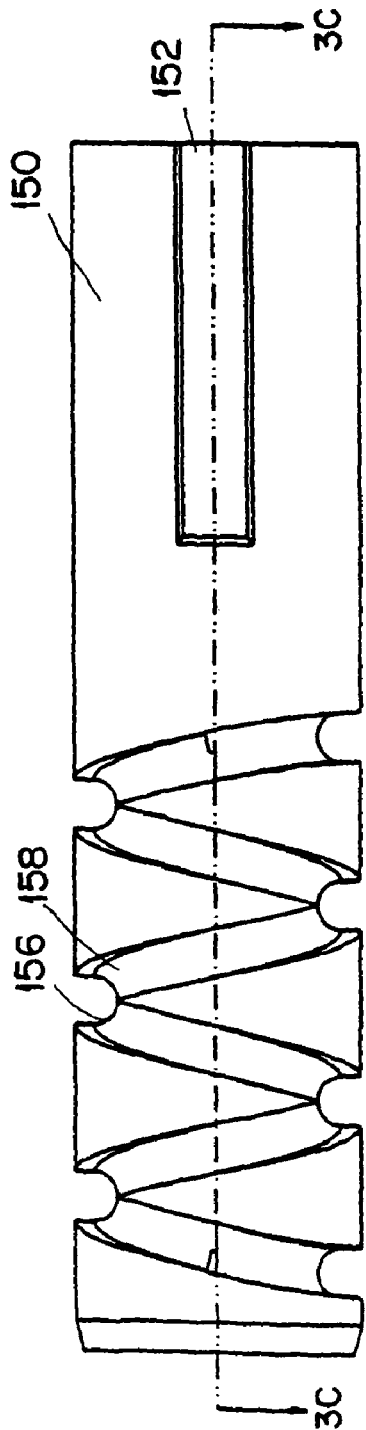
FIG. 3A is a top view.

As shown in FIGS. 1A and 1B, a cutting device 100 includes a driving end 110 and a cutting end 190. The driving end 110 is located at the proximal end of the cutting device 100. The cutting end 190 is located at the distal end of the cutting device 100.

At the driving end 110, there is an inner drive hub 130 with a drive coupler 120, and an outer hub 140. The drive coupler 120 mounts into a rotary driver (not shown), which turns the drive coupler 120 causing a helical member 150 and the inner drive hub 130 to rotate. For instance, the rotary driver is Dyonics Power Handpiece, No. 725355. The inner drive hub 130 with the drive coupler 120 is, for example, a component of Smith & Nephew disposable arthroscopic surgical instrument, No. 7205306. The helical member 150 is located within the inner drive hub 120 and the outer hub 140. The helical member 150 and a translation piece 145 are coupled together such that rotation of the helical member 150 causes linear translation of the helical member 150, as described further below.

The cutting device 100 includes an elongated inner member 185 and an elongated outer member 186, as shown in FIG. 1B. The inner member 185 is tubular with a hollow interior 184. The inner member 185 is fixed to the helical member 150 for axial and rotary motion therewith.

The outer member 186 is also tubular with a hollow interior 187. The inner member 185 is received inside the outer member 186. The outer member 186 is fixed to the outer hub 140 and does not move. The outer member 186 includes a tip 188, which is blunt, i.e., the corners are rounded. At the cutting end 190, the outer member 186 defines a cutting window 170 through a wall 186a of the outer member 186.

Referring to FIGS. 2A-2D, the inner drive hub 130 includes the drive coupler 120, a lumen 136, an aspiration opening 132, and a slot 134. The drive coupler 120 extends from the proximal end of the inner drive hub 130 and mounts in the rotary driver. Debris from the cutting end 190 of the cutting device 100 is aspirated through the aspiration opening 132. The slot 134 is disposed in a wall 131 of the inner drive hub 130. The slot 134 is like a track along one side of the inner drive hub 130. The slot 134 of the inner drive hub 130 is coupled with a key 152 of the helical member 150 (see FIG. 4B) so that rotation of the inner drive hub 130 causes the helical member 150 to rotate while allowing the helical member 150 to move axially relative to the inner drive hub 130, e.g., the key 152 axially slides along the slot 134.

Referring to FIGS. 3A-3D, the helical member 150 of the cutting device 100 is formed of a lubricious material in a tubular shape with a through lumen 159. The inner member 185 is disposed within the helical member 150 and fixed therein, for example, by epoxy, injection-molded, or overmolded plastic.

Figure 3B:
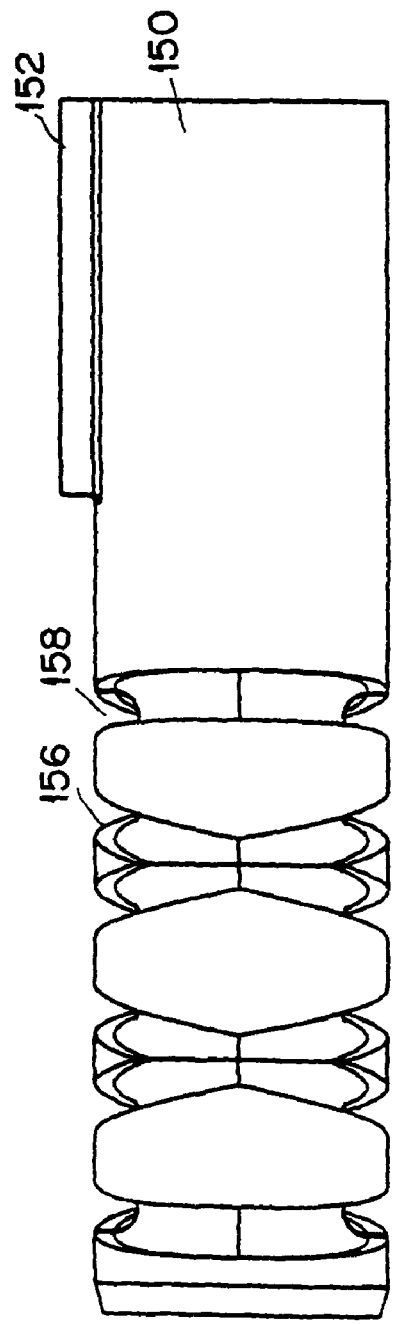
FIG. 3B is a side view.

The helical member 150 includes the key 152 and two helical channels 156, 158 disposed thereon. As shown in FIG. 3B, the key 152 is shaped like a fin and is located at the proximal end of the helical member 150. The key 152 mates with the slot 134 of the inner drive hub 130.

The two helical channels 156, 158 are disposed on a distal portion of the exterior surface of the helical member 150. One helical channel 156 is right-hand threaded; the other helical channel 158 is left-hand threaded. The pitch of the helical channels may be different or the same. The length of the distal portion of the helical member 150 with helical channels 156, 158 is longer than the length of the cutting window 170. The helical channels 156, 158 are smoothly blended together at their ends to form a continuous groove so that there is a smooth transition from one helical channel to the other helical channel at each end of the distal portion of the helical member 150.

The helical member 150 and the inner drive hub 130 are mechanically driven by the rotary driver. The helical member 150 also moves in an axial direction, e.g., reciprocates, as a result of the interaction of the translation piece 145 with the helical channels 156, 158, as described below.

Figure 4A:
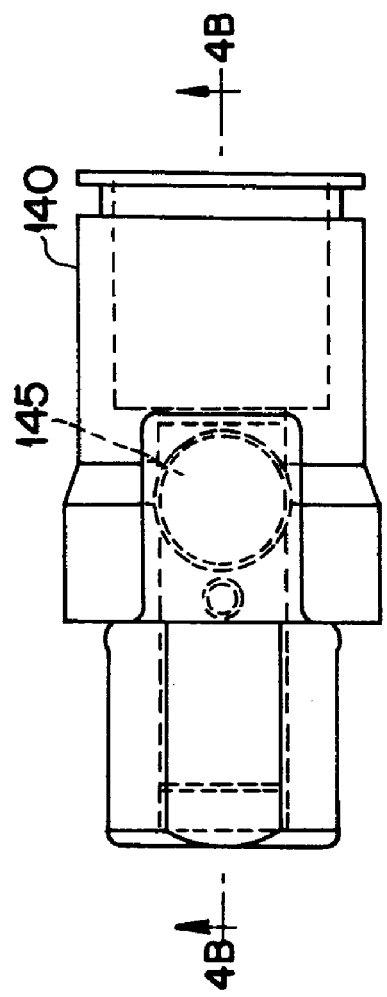
FIG. 4A is a top view.
Figure 4B:
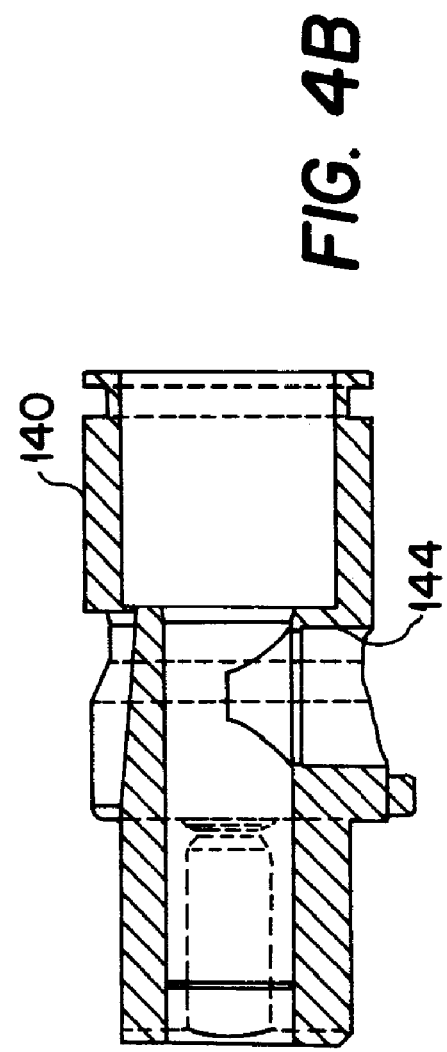
FIG. 4B is a cross-sectional view taken along 4B-4B in FIG. 4A.
Figure 4C:
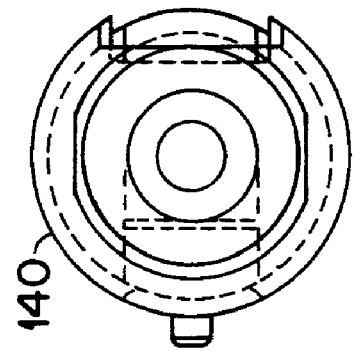
FIG. 4C is a distal end of the outer hub of the reciprocating rotary surgical instrument of FIG. 1.

Referring to FIGS. 4A-4C, the outer hub 140 of the cutting device 100 is formed of hard plastic and does not move. An example of an outer hub is a component of Smith & Nephew disposable arthroscopic surgical instrument, No. 7205306, modified with a cutout 144 for receiving the translation piece 145. The cutout 144 is disposed within a wall of the outer hub 140, for example, centrally, as in FIG. 4B, and aligned with the helical member. The translation piece 145 is located in the cutout 144 of the outer hub 140.

As shown in FIG. 1B, the outer member 186 is disposed within the outer hub 140 and fixed therein by a coupling 144 using, for example, epoxy, glue, insert molding, or spin-welding.

Figure 5A:
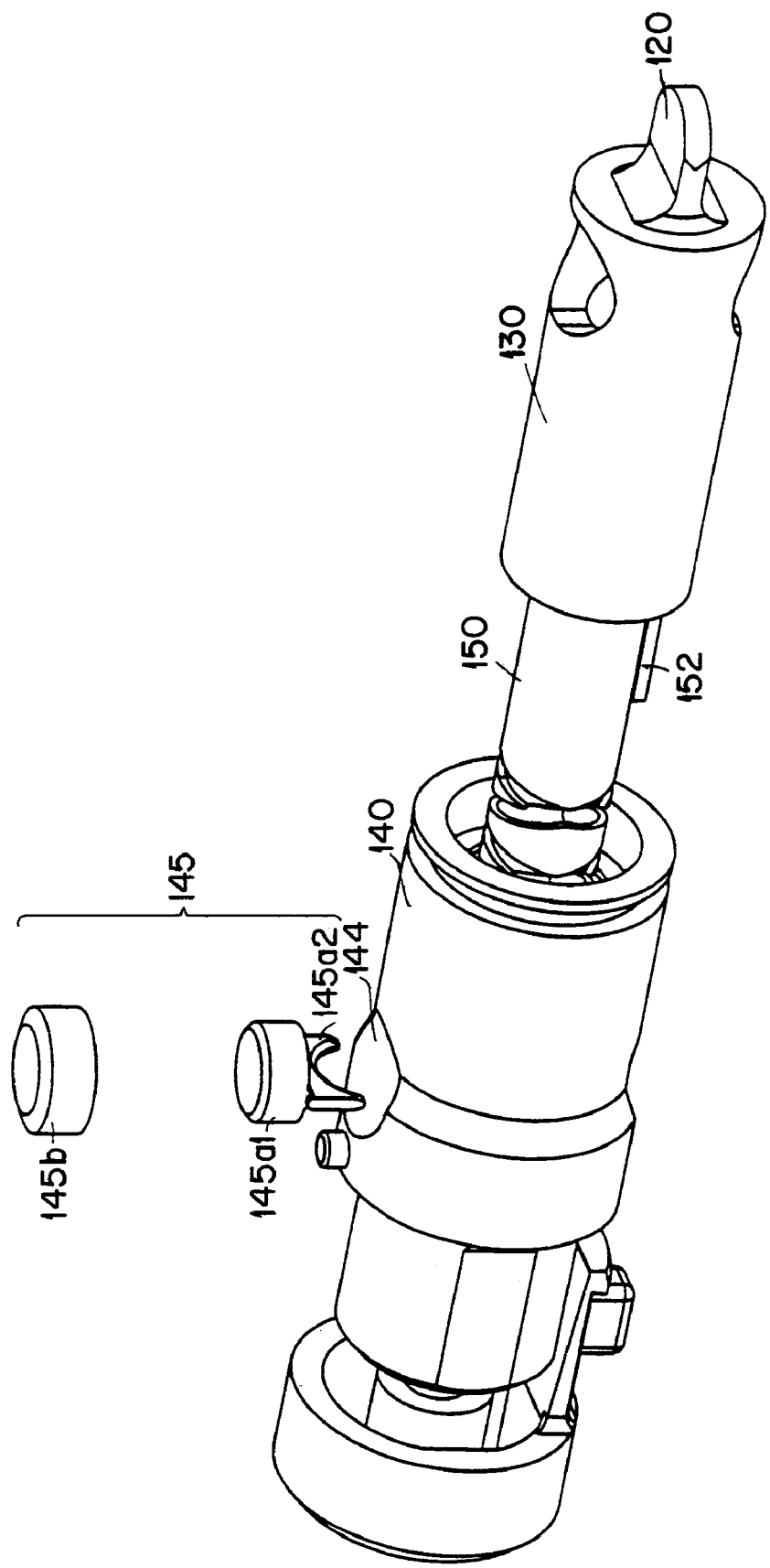
FIG. 5A is an exploded view.

Referring to FIG. 5A, the translation piece 145 includes a follower 145a and a cap 145b. Having the two helical channels 156, 158 in conjunction with the slot/key 134, 152 coupling of the inner drive hub 130 and the helical member 150, the rotary driver only needs to rotate in one direction and does not require reversal of the rotational direction upon the translation piece 145 reaching the end of one of the helical channels 156, 158.

Figure 5B:
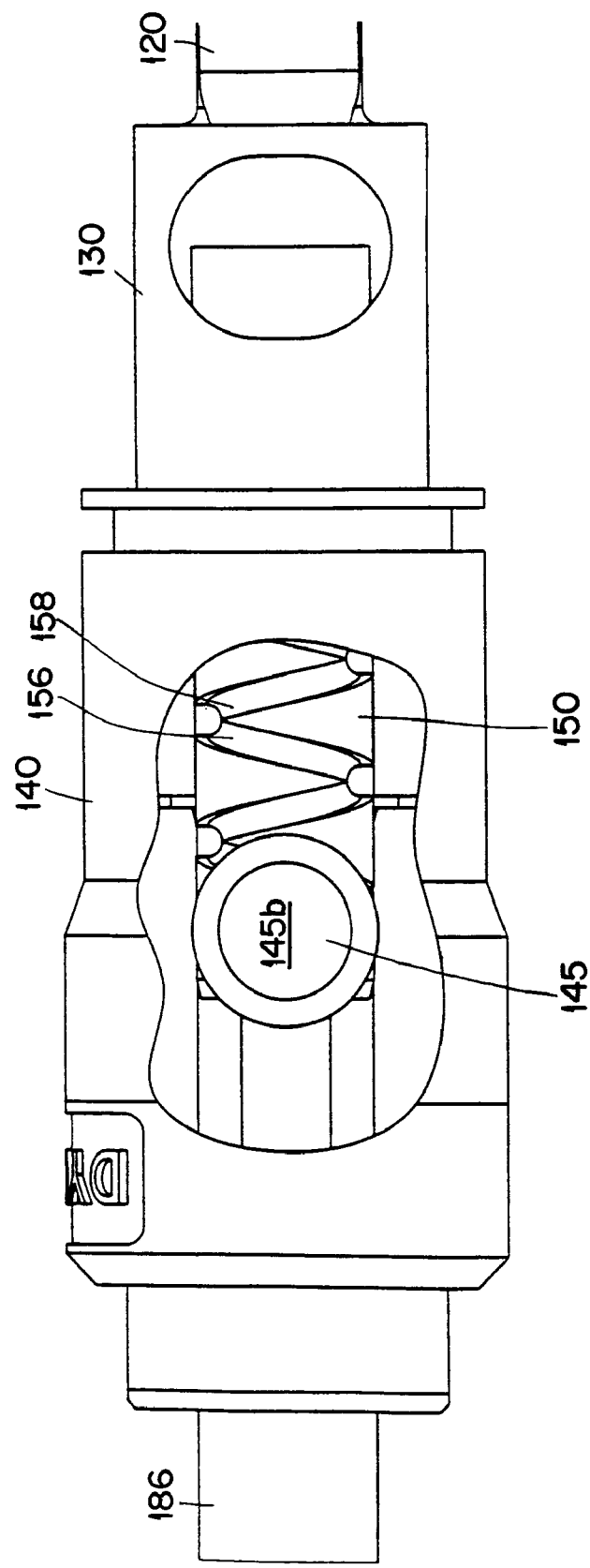
FIG. 5B is a partial cutaway view.
Figure 5C:
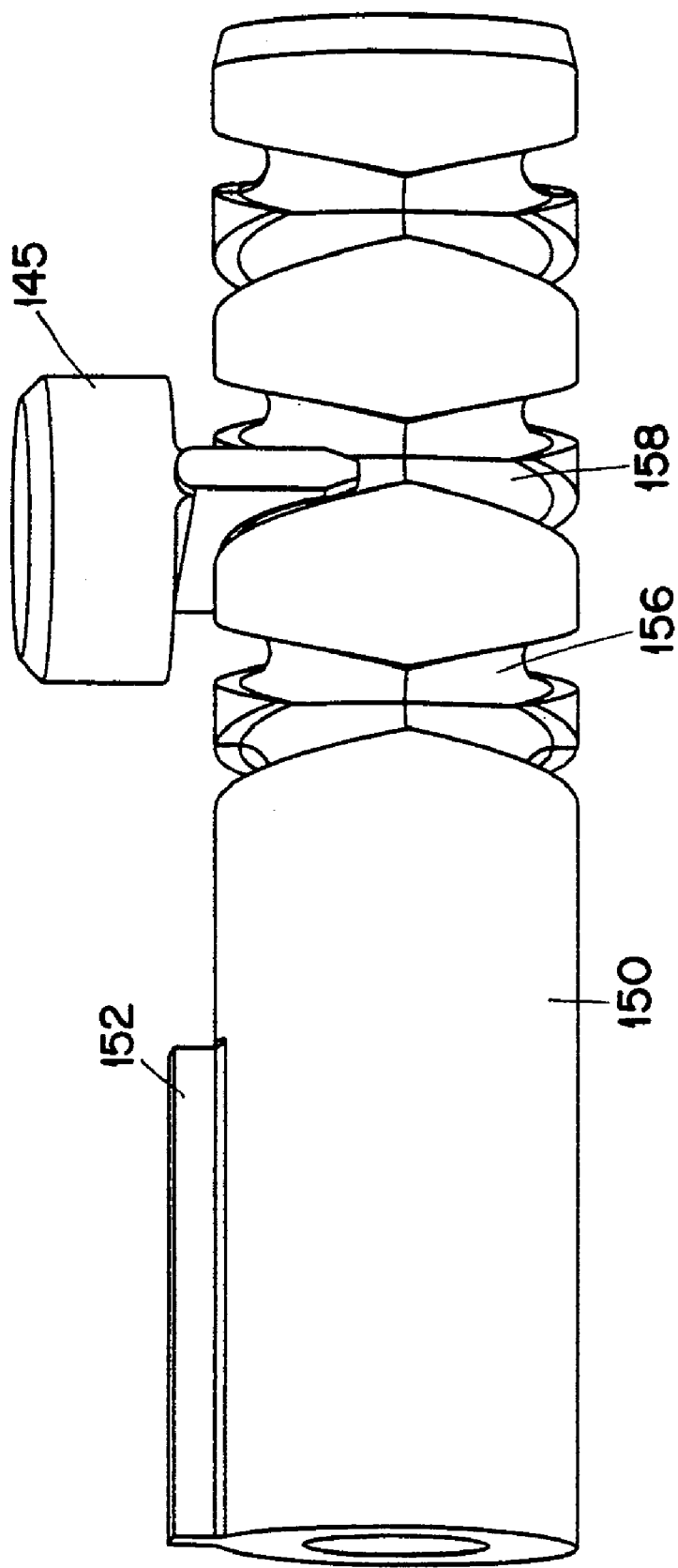
FIGS. 5C and 5D are side views of the translation piece and the helical member of the surgical instrument of FIG. 1.
Figure 5D:
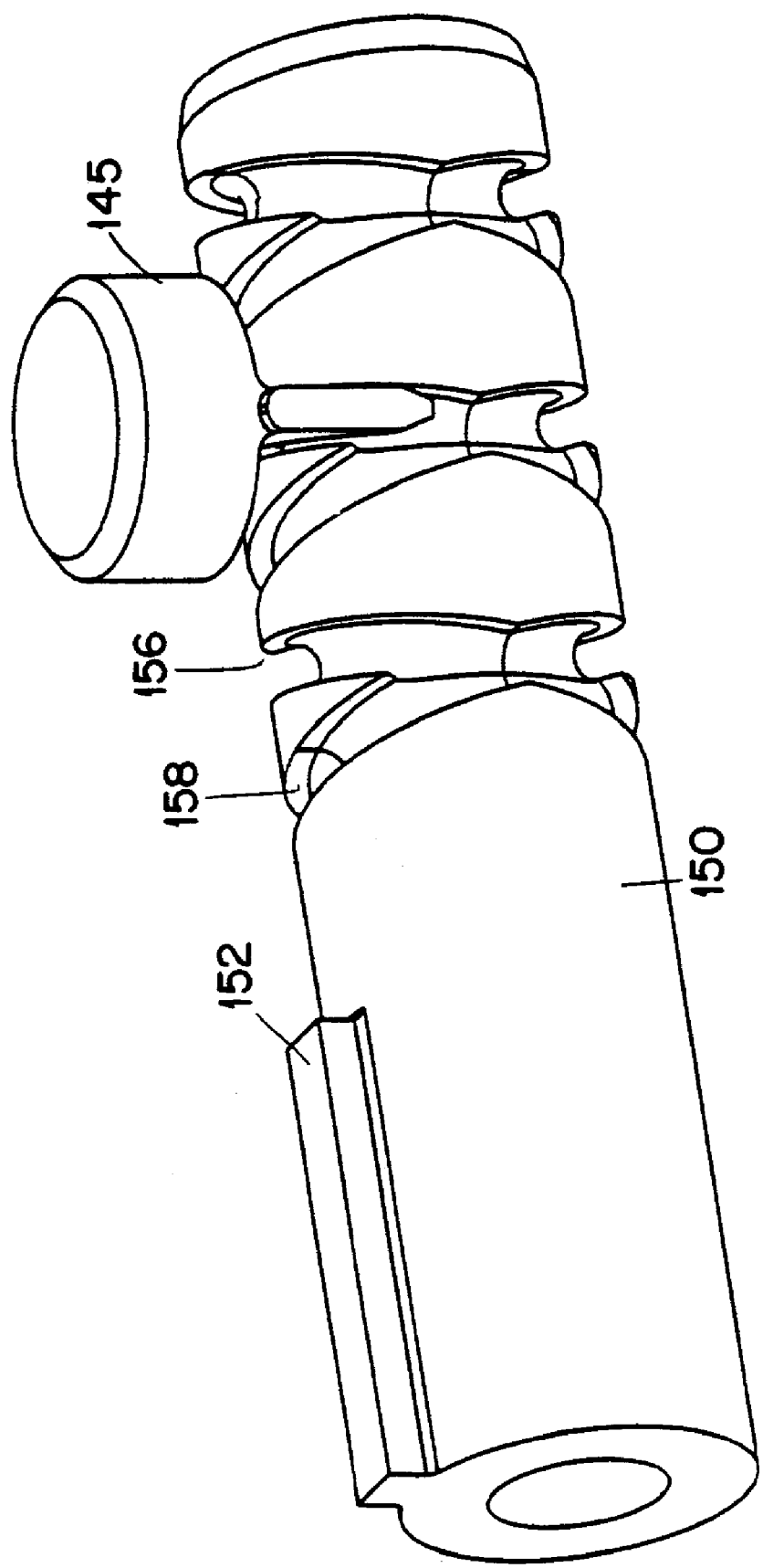

Referring to FIGS. 6A-6C, the follower 145a includes a cylindrical head 145a1 and two legs 145a2. As shown in FIGS. 5B-5D, the legs 145a2 form an arch and rest in the channels of the double helix 156, 158 formed in the distal portion of the exterior surface of the helical member 150. The arch of the legs 145a2 is dimensionally related to the diameter described by the helical channels 156, 158 of the helical member 150.

Referring particularly to FIGS. 5C and 5D, as the helical member 150 and the inner drive hub 130 are mechanically driven by the rotary driver (not shown), the follower 145a follows the helical channels 156, 158, swiveling as the follower 145a smoothly transitions from helical channel to helical channel 156,158 at the ends of the distal portion of the helical member 150 having the helical channels 156, 158. The coupling of the follower 145a to the helical channels 156, 158 causes the helical member 150 to also translate. Thus, the inner member 185 simultaneously rotates and reciprocates to cut the tissue.

Figure 7B:
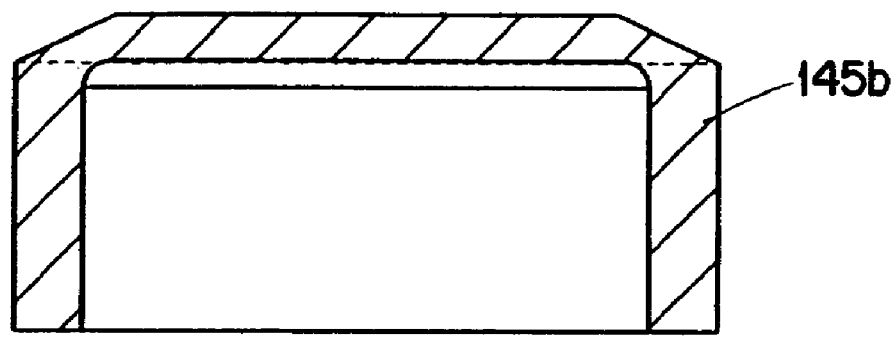
FIG. 7A is a top view and FIG. 7B is a cross-sectional view taken along 7B-7B of FIG. 7A of the cap for the follower of the translation piece of the reciprocating rotary surgical instrument of FIG. 1.
Figure 7A:
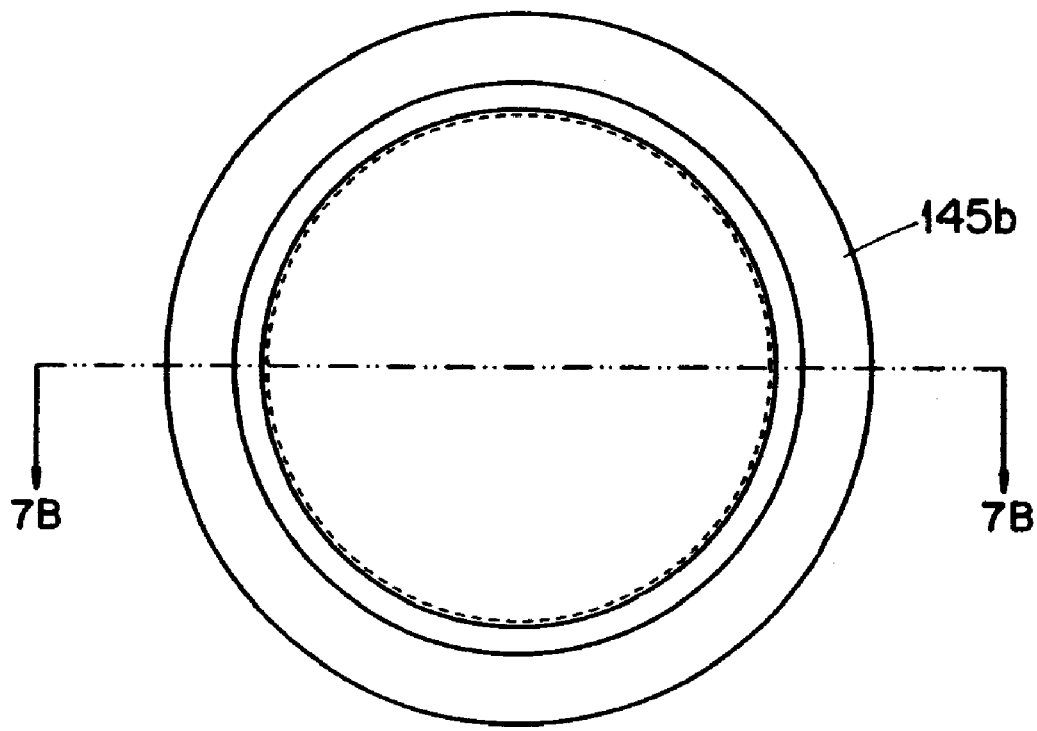

Referring to FIGS. 7A and 7B, the cap 145b of the translation piece 145 covers the follower 145a to provide a seal to allow sufficient suction to remove aspirated debris. Also, the cap 145b is a separate piece from the follower 145a in order to allow the follower 145b to swivel.

As shown in FIGS. 8A and 8B, the outer member cutting window 170 has a generally oblong shape. The proximal end 172 of the cutting window 170 is U-shaped and the distal end 173 has a saddle shape that forms a hook 174. The distal end 173 is chamfered to provide a sharp edge. The hook 174 pierces the targeted tissue to hold the tissue as the inner member 185 cuts. Also, the shape of the cutting window 170 eliminates galling between the inner and outer members 185, 186, and dulling of the cutting edge of the inner member 185.

The cutting window 170 is disposed proximate to the tip 188 of the outer member 186. The cutting window 170 exposes the inner member 185 over a length L.

Figure 10:
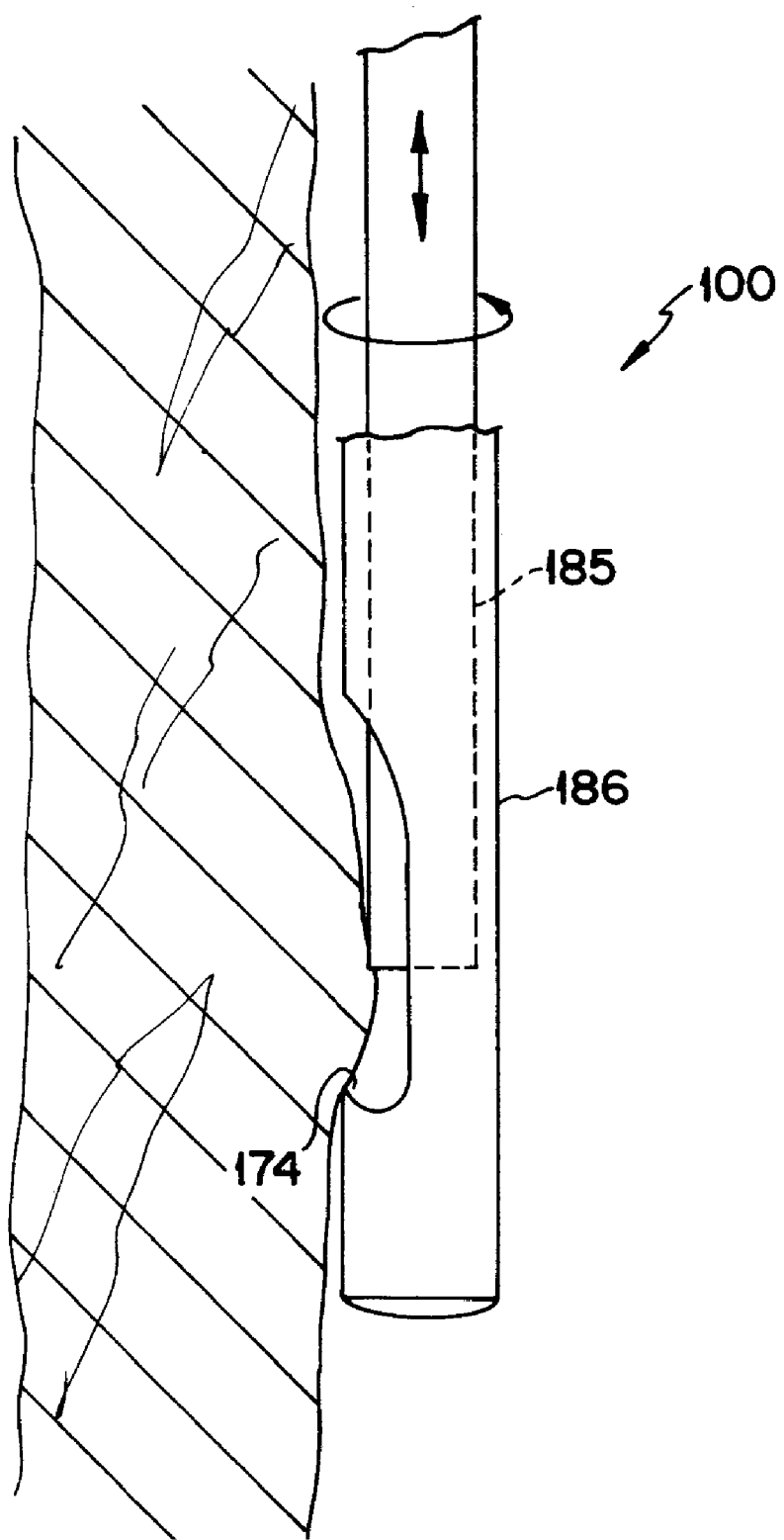
FIG. 10 illustrates a reciprocating rotary surgical instrument of FIG. 1 in use to cut tissue.

FIG. 9 shows that the inner member 185 is generally tubular with hollow interior 187. Aspiration of debris occurs through the hollow interior 187 of the inner member 185, and through the lumen of the helical member to the aspiration opening 132 of the inner drive hub 130. The distal end 183 of the inner member 185 is chamfered to a sharp edge 187 for cutting. The inner member 185 simultaneously rotates about its axis and translates along its axis to cut tissue. The cutting surface of the distal end 183 of the inner member 185 shears the tissue. For example, referring to FIG. 10, the cutting device 100 is placed tangentially against the targeted tissue such that the cutting window 170 exposes the inner member 185 to the tissue. As the inner member 185 rotates and translates, as shown by the arrows, the tissue within the cutting window catches on the hook 174 to initiate the cut and then the cutting edge 183 of the inner member 185 shears the tissue as the inner member 185 advances to cut the tissue. The cut is completed as the cutting edge 183 of the inner member 185 advances beyond the hook 174 of the cutting window 170 within the outer member 186.

FIG. 11 shows an alternative implementation of the inner member. The distal end 283 of the inner member 285 may be angled to a chamfered point so that the cut in the targeted tissue is initiated on one side and then extends across the width of the tissue. Similarly, when the cutting device is placed tangentially against the targeted tissue, the rotating and translating inner member 285 shears the tissue to be cut.

A number of implementations have been described. Nevertheless, it will be understood that various modifications may be made. For example, instead of a double helical channel, the helical member may include a single helical channel with a retractable follower and spring, or possibly, attraction and repelling forces of magnets or a solenoid could enable the rotating and reciprocating movements. Also, alternatively, the inner and outer members may have a cross-sectional shape other than circular. Additionally, the shape of the hook of the outer member may be modified in order to improve grasping of the tissue or grasping a larger volume of tissue. Accordingly, other implementations are within the scope of the following claims.

What is claimed is:

1. A surgical instrument, comprising:
    a cutting member including an implement for cutting tissue and defining a hollow interior; and
    a drive coupled to the cutting member to simultaneously rotate, translate, and reciprocate the cutting member in response to a rotational force applied to the drive and to cut tissue during simultaneous rotation and translation of the cutting member;
    wherein the drive includes:
        a drive member attached to the cutting member and including a lumen that is fluidly coupled to the hollow interior of the cutting member, and
        an inner drive hub coupled to the drive member and including an opening that communicates with the lumen of the drive member.

2. A surgical instrument, comprising:
    a cutting member configured to rotate and translate to cut tissue, and configured to aspirate cut tissue and fluid therethrough;
    a helical drive member coupled to the cutting member to impart simultaneous translation and rotation to the cutting member;
    a translation piece configured and arranged to engage the helical drive member such that the helical drive member simultaneously rotates and translates in response to a force applied thereto; and
    a driver coupled to the helical drive member to provide the force, wherein the driver rotates and rotation of the driver in a single direction causes simultaneous translational reciprocation and rotation of the cutting member.

3. The surgical instrument of claim 2, wherein the cutting member comprises an outer tubular member and an inner tubular member received within the outer tubular member, the inner tubular member configured to translate and rotate relative to the outer tubular member.

4. A surgical instrument, comprising:
    an inner tubular member having an open distal tip and including an implement for cutting tissue at the distal tip, the inner tubular member configured and arranged in use for aspiration of cut tissue therethrough through the open distal tip and along the entire inner tubular member, the implement having a distal cutting edge;
    a power-driven drive coupled to the implement for cutting tissue to simultaneously rotate, translate, and reciprocate the implement in response to only rotation force applied to the drive and to cut tissue during simultaneous rotation and translation of the implement, wherein the drive includes a first member that is rotatable in response to the rotation force and a second member coupled to the first member such that rotation of the first member results in reciprocation of the inner tubular member through the interaction between the first member and the second member, a longitudinal axis of the inner tubular member and a longitudinal axis defined by the first member being aligned in parallel; and
    an outer tubular member, the inner tubular member being received within the outer tubular member, the outer tubular member having a closed distal tip and a cutting window disposed proximate to the tip of the outer tubular member, the cutting window exposing the inner tubular member to tissue such that tissue enters the open distal tip of the inner tubular member through the cutting window.

5. A surgical instrument, comprising:
    an inner tubular member having an open distal tip and including an implement for cutting tissue at the distal tip, the inner tubular member configured and arranged for aspiration of cut tissue therethrough through the open distal tip and along the inner tubular member, the implement having a distal cutting edge;
    a power-driven drive coupled to the implement for cutting tissue to simultaneously rotate, translate, and reciprocate the implement in response to only rotation force applied to the drive and to cut tissue during simultaneous rotation and translation of the implement, wherein the drive includes a first member that is rotatable in response to the rotation force and a second member coupled to the first member such that rotation of the first member results in reciprocation of the inner tubular member through the interaction between the first member and the second member, a longitudinal axis of the inner tubular member and a longitudinal axis defined by the first member being aligned in parallel; and a stationary outer tubular member, the inner tubular member being received within the outer tubular member, the outer tubular member having a closed distal tip and a cutting window disposed proximate to the tip of the outer tubular member, the cutting window exposing the inner tubular member to tissue such that tissue enters the open distal tip of the inner tubular member through the cutting window.

6. A surgical instrument, comprising:

a cutting member including an implement for cutting tissue; and a drive coupled to the cutting member to simultaneously rotate, translate, and reciprocate the cutting member in response to only a rotational force applied to the drive in a single direction and to cut tissue during simultaneous rotation and translation of the cutting member, wherein the drive includes a drive member attached to the cutting member, the drive member including a helical groove, and the drive includes a translation piece disposed in the groove such that rotary driving of the drive member results in simultaneous rotation and reciprocation of the cutting member.

* * * * *

UNITED STATES PATENT AND TRADEMARK OFFICE
CERTIFICATE OF CORRECTION

| | | |
|---|---|---|
| PATENT NO. | : 7,922,737 B1 | |
| APPLICATION NO. | : 11/734674 | |
| DATED | : April 12, 2011 | |
| INVENTOR(S) | : Peter M. Cesarini et al. | |

It is certified that error appears in the above-identified patent and that said Letters Patent is hereby corrected as shown below:

On the Title page, column 1, section "(75) Inventors", replace "Cassidy," with
--Cassidy Jr.,--.

Signed and Sealed this
Thirty-first Day of January, 2012

David J. Kappos
*Director of the United States Patent and Trademark Office*